United States Patent [19]
Teraoka et al.

[11] Patent Number: 5,459,064
[45] Date of Patent: Oct. 17, 1995

[54] PROTEASE

[75] Inventors: Hiroshi Teraoka, Osaka; Mikio Tamaki, Nara; Etsuo Nakamura; Masaru Shin, both of Kobe; Nobuo Yoshida, Nishinomiya; Hiroshige Tsuzuki, Tsuzuki; Takashi Fujiwara, Nara; Koichi Matsumoto, Osaka, all of Japan

[73] Assignee: Shionogi & Co., Ltd., Osaka, Japan

[21] Appl. No.: 35,634

[22] Filed: Mar. 23, 1993

Related U.S. Application Data

[62] Division of Ser. No. 782,372, Oct. 24, 1991, abandoned.

[30] Foreign Application Priority Data

Oct. 24, 1990 [JP] Japan .................. 2-288110

[51] Int. Cl.⁶ ................... C12N 15/11; C12N 15/52
[52] U.S. Cl. .................. 435/252.31; 435/252.3; 435/320.1; 536/23.2
[58] Field of Search .................. 435/836, 69.1, 435/252.5, 320.1; 536/27

[56] References Cited

U.S. PATENT DOCUMENTS 4,266,031  5/1981  Tang ........................ 435/188

FOREIGN PATENT DOCUMENTS 61-12287  1/1986  Japan .

OTHER PUBLICATIONS

Okada, J., et al., "Genetically engineered *Bacillus subtilis* for extracellular protease manufacture," *Chem Abstracts* (1986) 104(19): 164 (Abstract No. 163023). A copy of the corresponding Japanese Patent 61–12287 is also enclosed herewith.

Drapeau, G. R., et al., "Purification and Properties of an Extracellular Protease of *Staphylococcus aureus*", *J. Biol. Chem.* (1972) 247:6720–6726.

Carmona, C., et al., "Nucleotide Sequence of the Serine Protease Gene of *Staphylococcus aureus*, Strain V8", *Nucl. Acids Res.* (1987) 15(16):6757.

Yoshida, N., et al., "Purification and Characterization of an Acidic Amino Acid Specific Endopeptidase of *Streptomyces griseus* Obtained from a Commercial Preparation (Pronase)", *J. Biochem.* (1988) 104(3):451–456.

Niidome, T., et al., "Purification and Characterization of an Acidic Amino Acid–Specific Endopeptidase of *Bacillus subtilis* Obtained from a Commercial Preparation (Protease Type XVI, Sigma)", *J. Biochem.* (1990) 108:965–970.

Stahl et al., "Confirmation of Protoplast Fusion–Derived Linkages in *Staphylococcus aureus* by Transformation with Protoplast DNA", *J. Bacteriol,* (1983) 154(1):406–412.

Stahl et al., "Replacement of the *Bacillus subtilis* Subtilisin Structural Gene with an In Vitro–Derived Deletion Mutation", *J. Bacteriol.* (1984) 158(2):411–418.

Vitkovic, L., et al., "Purification of the Extracellular Protease of Bacillus licheniformis and Its Inhibition by Bacitracin", *J. Bacteriol.* (1977) 131(3):891–896.

Akparov, V., et al., "Extracellular Serine Proteinase from *Bacillus licheniformis*", *Chemical Abstracts* (1983) 98(9), p. 252, Abstract No. 98:67639g.

European Patent Application Sequence Listing Abstract R14159 A–Gene Sequence 7. (This publication was cited by Examiner Schmikel with Paper #10 for the related application, Ser. No. 07/782,372).

Suggs et al *Proc Natl. Acad Sci USA* 78 No. 11. pp. 6613–6617 Nov 1981.

*Primary Examiner*—Mindy B. Fleisher
*Attorney, Agent, or Firm*—Morrison & Foerster

[57]  ABSTRACT

A novel protease derived from *Bacillus licheniformis* is provided. The protease cleaves the peptide bonds at the carboxyl termini of glutamic acid residues in polypeptides. The protease contains an amino acid sequence from serine in the +1 position to glutamine in the +222 position of SEQ ID NO: 1.

11 Claims, 6 Drawing Sheets

```
  1   T CGA CGG CTT CCC GTG CGC CTC CGG GAT CGC TGT GAT AAT TGA CAA
              ─────────────────────────►
                  SENSE PRIMER (C)
 47   CCA CAT TCA TCT TTT CTT TTC CAA ACC GTT CTG CAA CCG CCT TGC CTA

95   TAC CTT TTG AAG AGC CGG TCA CAA TTG CTG TTT TTC CTT TTA AAT CAC

143   TAT ACA ACC TAA ACA CCC CTC AAT TTC TTT TCT CCA TGT ACA TTA CCC

191   GGT ATC AAT ATA TGA TCA AAC AAA ATG TTA ATA CAC ACC TTT AGT ATG

239   ATC TTT TTT AAA CAT ATG GAA AAT TCA GAA TTA TTT TGT TAA TAT CTA

287   ACT TGT ACT TAC AAC AAA ATA AGG AAG TGA TAT GAT TTG GTT AGT AAA
                                                          (-94)
  1                                                       fMet Val Ser Lys

335   AAG AGT GTT AAA CGA GGT TTG ATC ACA GGT CTC ATT GGT ATT TCT ATT
          (-90)                                   (-80)
  5   Lys Ser Val Lys Arg Gly Leu Ile Thr Gly Leu Ile Gly Ile Ser Ile

383   TAT TCT TTA GGT ATG CAC CCG GCC CAA GCC GCG CCA TCG CCT CAT ACT
                      (-70)                                   (-60)
 21   Tyr Ser Leu Gly Met His Pro Ala Gln Ala Ala Pro Ser Pro His Thr

431   CCT GTT TCA AGC GAT CCT TCA TAC AAA GCG GAA ACA TCG GTT ACT TAT
                              (-50)
 37   Pro Val Ser Ser Asp Pro Ser Tyr Lys Ala Glu Thr Ser Val Thr Tyr

479   GAC CCA AAC ATT AAG AGC GAT CAA TAC GGC TTG TAT TCA AAA GCG TTT
          (-40)                                       (-30)
 53   Asp Pro Asn Ile Lys Ser Asp Gln Tyr Gly Leu Tyr Ser Lys Ala Phe

527   ACA GGC ACC GGC AAA GTG AAT GAA ACA AAG GAA AAA GCG GAA AAA AAG
                              (-20)
 69   Thr Gly Thr Gly Lys Val Asn Glu Thr Lys Glu Lys Ala Glu Lys Lys
```

FIG. 1-1

```
575 TCA CCC GCC AAA GCT CCT TAC AGC ATT AAA TCG GTG ATT GGT TCT GAT
    (-10)                                (-1)  1
 85 Ser Pro Ala Lys Ala Pro Tyr Ser Ile Lys Ser Val Ile Gly Ser Asp

623 GAT CGG ACA AGG GTC ACC AAC ACA ACC GCA TAT CCG TAC AGA GCG ATC
                    10  BL8                                 20
101 Asp Arg Thr Arg Val Thr Asn Thr Thr Ala Tyr Pro Tyr Arg Ala Ile

671 GTT CAT ATT TCA AGC AGC ATC GGT TCA TGC ACC GGA TGG ATG ATC GGT
                                30
117 Val His Ile Ser Ser Ser Ile Gly Ser Cys Thr Gly Trp Met Ile Gly

719 CCG AAA ACC GTC GCA ACA GCC GGA CAC TGC ATC TAT GAC ACA TCA AGC
    B40 40                                          50
133 Pro Lys Thr Val Ala Thr Ala Gly His Cys Ile Tyr Asp Thr Ser Ser

767 GGT TCA TTT GCC GGT ACA GCC ACT GTT TCG CCG GGA CGG AAC GGG ACA
                        60                                       70
149 Gly Ser Phe Ala Gly Thr Ala Thr Val Ser Pro Gly Arg Asn Gly Thr

815 AGC TAT CCT TAC GGC TCA GTT AAA TCG ACG CGC TAC TTT ATT CCG TCA
                                80
165 Ser Tyr Pro Tyr Gly Ser Val Lys Ser Thr Arg Tyr Phe Ile Pro Ser

863 GGA TGG AGA AGC GGA AAC ACC AAT TAC GAT TAC GGC GCA ATC GAA CTA
                    90                                  100
181 Gly Trp Arg Ser Gly Asn Thr Asn Tyr Asp Tyr Gly Ala Ile Glu Leu

911 AGC GAA CCG ATC GGC AAT ACT GTC GGA TAC TTC GGA TAC TCG TAC ACT
                            110
197 Ser Glu Pro Ile Gly Asn Thr Val Gly Tyr Phe Gly Tyr Ser Tyr Thr

959 ACT TCA TCA CTT GTT GGG ACA ACT GTT ACC ATC AGC GGC TAC CCA GGC
        120             B125                        130
213 Thr Ser Ser Leu Val Gly Thr Thr Val Thr Ile Ser Gly Tyr Pro Gly

1007 GAT AAA ACA GCA GGC ACA CAA TGG CAG CAT TCA GGA CCG ATT GCC ATC
     BL83        140                                 150
229  Asp Lys Thr Ala Gly Thr Gln Trp Gln His Ser Gly Pro Ile Ala Ile
```

FIG. 1-2

```
1055 TCC GAA ACG TAT AAA TTG CAG TAC GCA ATG GAC ACG TAC GGA GGA CAA
                                        160
 245 Ser Glu Thr Tyr Lys Leu Gln Tyr Ala Met Asp Thr Tyr Gly Gly Gln

1103 AGC GGT TCA CCG GTA TTC GAA CAA AGC AGC TCC AGA ACG AAC TGC AGC
             170                                     180
 261 Ser Gly Ser Pro Val Phe Glu Gln Ser Ser Ser Arg Thr Asn Cys Ser

1151 GGT CCG TGC TCG CTT GCC GTA CAC ACA AAT GGA GTA TAC GGC GGC TCC
                                 190
 277 Gly Pro Cys Ser Leu Ala Val His Thr Asn Gly Val Tyr Gly Gly Ser

1199 TCG TAC AAC AGA GGC ACC CGG ATT ACA AAA GAG GTG TTC GAC AAT TTG
         200                                     210
 293 Ser Tyr Asn Arg Gly Thr Arg Ile Thr Lys Glu Val Phe Asp Asn Leu

1247 ACC AAC TGG AAA AAC AGC GCA CAA TAA TAC ACG AAG ACA GCC CGC TTC
                         220     222                  ─────────────
 309 Thr Asn Trp Lys Asn Ser Ala Gln ***              TERMINATOR

1295 CTT TTG GAA CGG GCT GTC ACA TCT AAC GGC CGT ATA CTT AAT TTC CTT
     ─── ───────────────────
      →  ←

1343 TAA GCC TGT ACT TTT TGC CAT CTA TTG ATA TCG TGA AAT TTG AAG GAC
                                                                 ───
                                                                  ←

1391 CGC TGA TCG GCA AAT AAT AGA CAA GCT GAA ACT CCG CTT CCT CAC CAG
     ─────────────────────
     ANTISENSE PRIMER (D)
1439 GTT TGA ATG G
```

FIG. 1-3

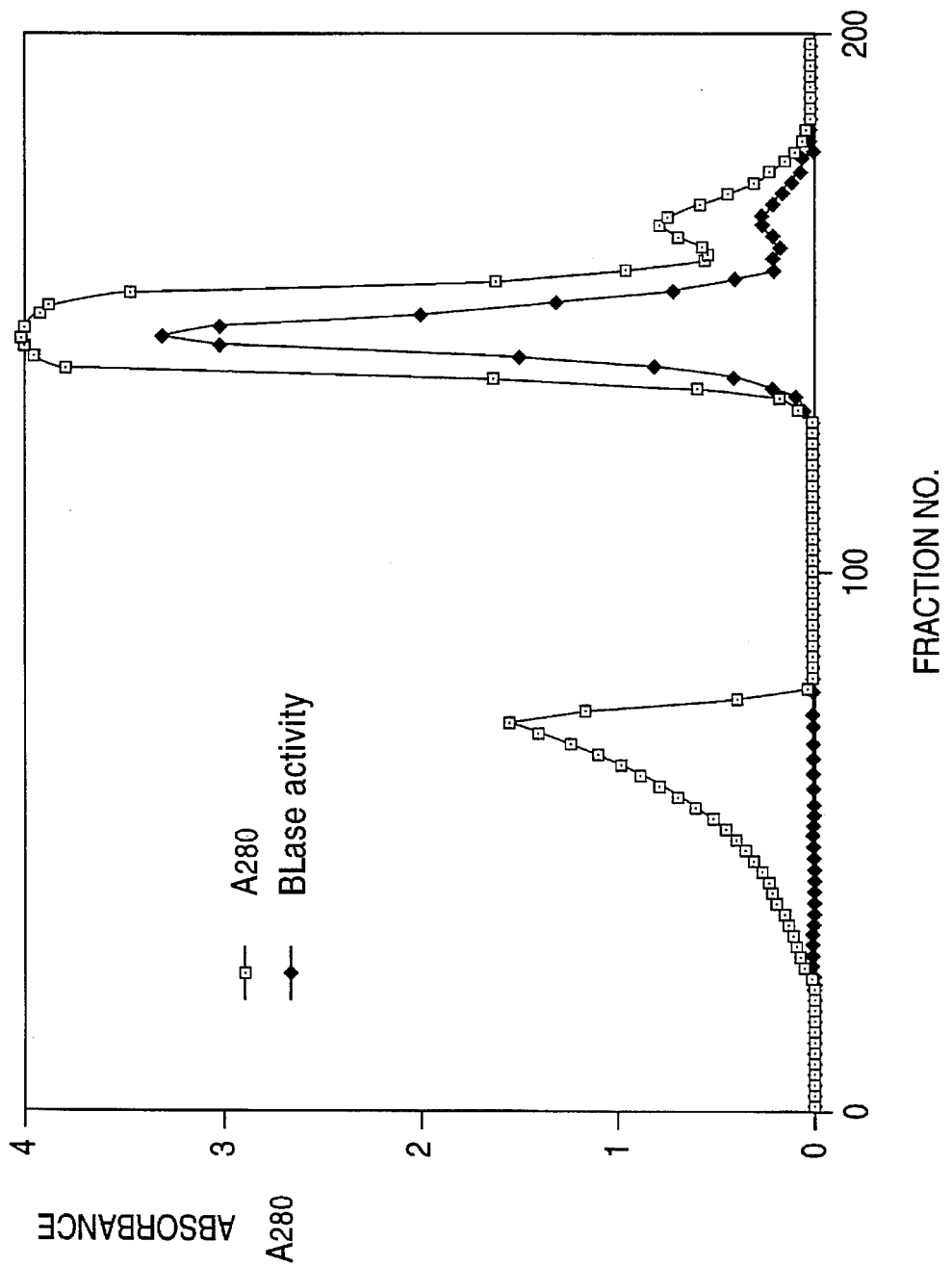

PROTEASE

CROSS REFERENCE

This application is a divisional of U.S. application Ser. No. 07/782,372 filed Oct. 24, 1991, now abandoned, which application is incorporated herein by reference and to which application we claim priority under 35 USC §120 and is based on Japanese application 2-288110 filed Oct. 24, 1990, which application is incorporated herein by reference and to which application we claim priority under 35 USC §119.

BACKGROUND OF THE INVENTION

1. Field of the Invention

The present invention relates to a novel protease which specifically cleaves the peptide bond at the carboxyl termini of glutamic acid residues in the amino acid sequences of polypeptides, a method for producing the protease from bacteria of the genus Bacillus, a DNA sequence encoding the protease, an expression vector containing the DNA sequence, a transformant obtained by introducing this expression vector into a host, and a method for producing the protease using the transformant.

2. Description of the Prior Art

The V8 protease derived from the V8 strain of *Staphylococcus aureus* is already known as an enzyme which acts upon proteins (i.e., polypeptides) and specifically cleaves the peptide bond at the carboxyl terminal of glutamic acid (Glu) residues (Gabriel R. Drapeau et al., J. Biol. Chem. 247, 20, 6720–6726, 1972). This enzyme is classified as a serine protease. C. Carmona et al. have cloned the DNA sequence encoding this enzyme (Nucl. Acids Res., 15, 6757, 1987).

A similar enzyme, an endopetidase which is specific for acidic amino acid residue and is derived from an actinomycete bacterium *Streptomyces griseus*, is also known (Norio Yoshida et al., J. Biochem. 104, 3, 451–456, 1988). Furthermore, an endoprotease which is specific for glutamic acid residue derived from *Bacillus subtilis* is also known (Takuro Niidome, Norio Yoshida, Fusahiro Ogata, Akio Ito, and Kosaku Noda, J. Biochem. 108, 965–970, 1990); Abstracts of 62nd General Conference of the Japan Biochemical Society).

The aforesaid enzymes are useful when specific cleavage of proteins at the aforesaid sites is desired for the purposes of protein structural analysis, etc., or when recombinant DNA techniques have been employed to produce a desired protein in the form of a certain fusion protein, from which the desired protein is to be obtained by cleavage. In the latter case, for example, when the desired protein has been produced in the form of a fusion protein in which the desired protein is linked with another protein via a glutamic acid residue, the desired protein can be separated by cleavage with such an enzyme. For these reasons, the availability of other proteases possessing this type of enzymatic activity, in addition to those mentioned above, would be highly desirable.

SUMMARY OF THE INVENTION

The novel protease of this invention, which overcomes the above-discussed and numerous other disadvantages and deficiencies of the prior art, is derived from *Bacillus licheniformis*, and the protease cleaves the peptide bonds at the carboxyl termini of glutamic acid residues in polypeptides.

In a preferred embodiment, the protease is derived from *Bacillus licheniformis* ATCC No. 14580.

In a preferred embodiment, the protease has the following properties:

(1) Optimal pH: approximately 8.0, and (2) Stable pH range: pH 6.5–8.5 at 25° C.

In a preferred embodiment, the protease contains an amino acid sequence from serine in the +1 position to glutamine in the +222 position of SEQ ID NO: 1.

In a preferred embodiment, the protease contains an amino acid sequence from serine in the +1 position to glutamine in the +222 position of SEQ ID NO: 1, and cleaves the peptide bonds at the carboxyl termini of glutamic acid residues in polypeptides.

The DNA sequence of this invention encodes the above-mentioned protease.

In a preferred embodiment, the DNA sequence contains a base sequence from the thymine residue in the 605 position to the adenosine residue in the 1270 position of SEQ ID NO: 1.

In a preferred embodiment, the DNA sequence encodes a protease containing an amino acid sequence from N-formyl-methionine at the −94 position to the glutamine at the +222 position of SEQ ID NO: 1.

In a preferred embodiment, the DNA sequence contains a base sequence, from the thymine residue in the 323 position to the adenosine residue in the 1270 position, of SEQ ID NO: 1.

The expression vector of this invention contains the above-mentioned DNA sequence.

In a preferred embodiment, the expression vector is expressible in bacteria of the genus Bacillus.

The transformant of this invention is obtainable by introducing the above-mentioned expression vector into a host.

In a preferred embodiment, the host is a strain belonging to the genus Bacillus.

The method for producing a protease of this invention comprises the steps of cultivating a strain of *Bacillus licheniformis* capable of producing the above-mentioned protease in a culture medium and recovering the produced protease from the culture medium.

The method for producing a protease of this invention comprises the steps of cultivating the above-mentioned transformant in a culture medium and recovering the produced protease from the culture medium.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

Thus, the invention described herein makes possible the objectives of:

(1) providing a novel protease with an enzymatic activity of specifically cleaving polypeptides at the carboxyl termini of glutamic acid residues; and (2) providing a DNA sequence encoding the protease, an expression vector containing the DNA sequence, a transformant obtained by introduction of the expression vector into a host, and a method for the production of the protease using the transformant.

BRIEF DESCRIPTION OF THE DRAWINGS

This invention may be better understood and its numerous objects and advantages will become apparent to those skilled in the art by reference to the accompanying drawings as follows:

FIGS. 1—1 to 1-3 show the DNA sequence of the protease of the present invention and the amino acid sequence deduced from the DNA sequence.

FIG. 2 is a schematic diagram illustrating the construction of the expression vector pHY300BLtt of the present invention.

FIG. 3 is a schematic diagram illustrating the construction of the shuttle vector pHY300PLKtt used in the construction of the expression vector pHY300BLtt of the present invention.

FIG. 4 shows graphs indicating the elution of the enzyme of the present invention from an affinity column in the process of extraction and purification of the enzyme from the medium in which *Bacillus licheniformis* ATCC No. 14580 was cultivated.

DESCRIPTION OF THE PREFERRED EMBODIMENTS

Figure 2:
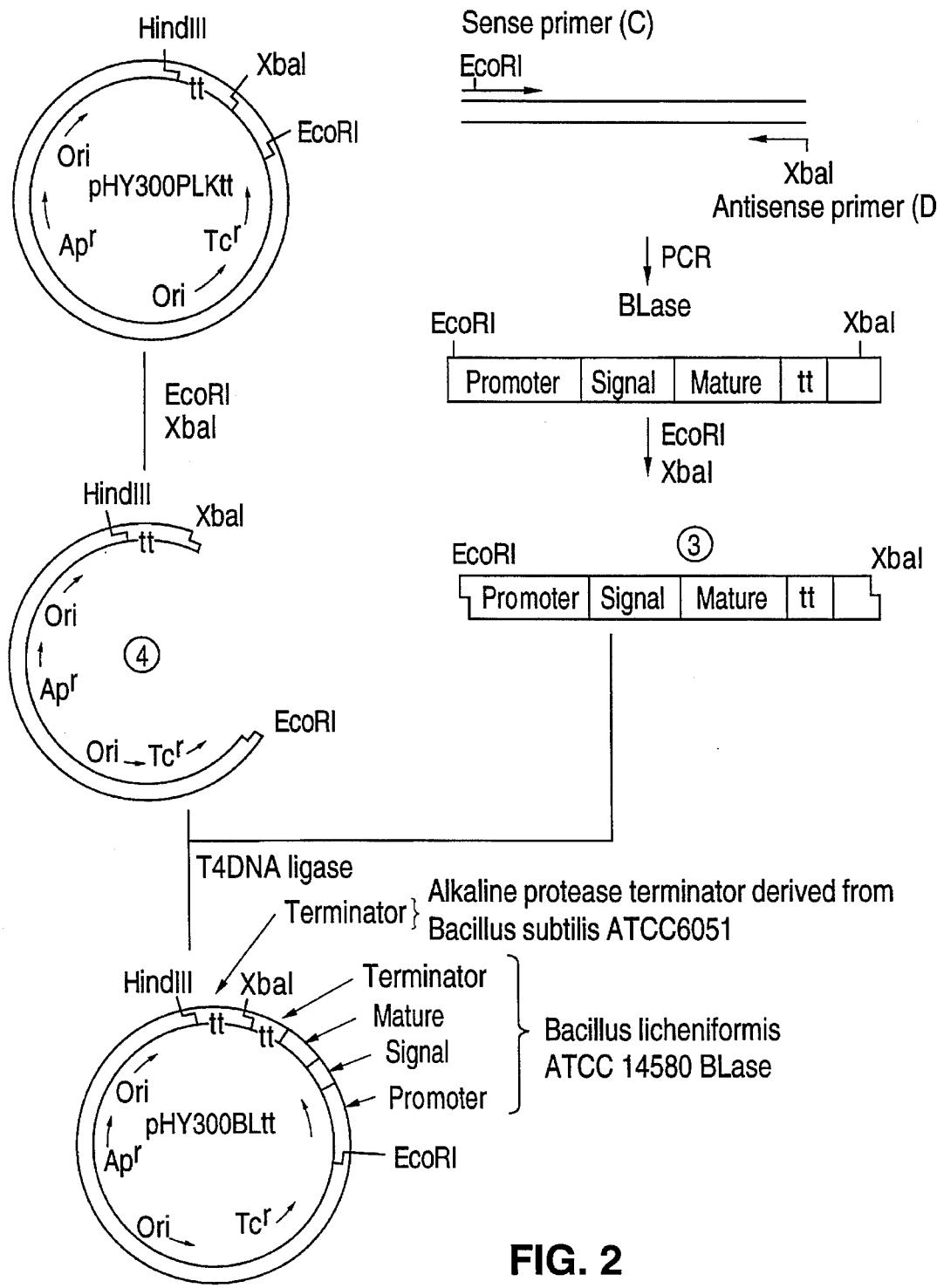

The present inventors have conducted various studies with a view to obtaining proteases, possessing the enzymatic action of cleaving peptides at the carboxyl termini of glutamic acid residues, from microorganisms other than the aforesaid *Staphylococcus aureus*, etc. As a result of these researches, the present inventors have discovered a novel protease possessing the aforesaid property, derived from *Bacillus licheniformis* ATCC No. 14580. Furthermore, the present inventors have also found a DNA sequence encoding this protease and created an expression vector containing the DNA sequence as well as transformant obtained by introduction of the expression vector into a host, and discovered a method for the production of this protease using the transformant, thereby completing the present invention.

The protease of the present invention (hereinafter referred to as BLase) is produced by bacteria of the genus Bacillus, in particular, by *Bacillus licheniformis* ATCC No. 14580. This strain is available from the American Type Culture Collection (ATCC).

I. Culture conditions

No special medium is required for the cultivation of the aforesaid bacterial strain, and any of the various conventional types of culture medium are suitable for this purpose. For example, a medium containing glucose, soybean powder, meat extract, corn steep liquor, and the various inorganic salts, etc., can be used. The appropriate medium pH is 5–9, preferably approximately 7.0, the appropriate medium temperature is 15°–50° C., preferably approximately 28° C., and the bacteria are cultured, for example, aerobically with stirring or shaking for approximately 36 hours. The enzyme BLase of the present invention was principally secreted extracellularly.

II. Collection of enzyme

Known processes for the collection and purification of enzymes can be used, either singly or in combination, for the collection and purification of the present enzyme from the aforesaid culture broth. For example, the culture broth can be subjected to filter pressing, ultrafiltration, and centrifugal separation, thereby obtaining a cell-free liquid concentrate. The enzyme of the present invention can then be obtained from this concentrate by an appropriate method of purification. For example, the aforesaid concentrate can be subjected first to preliminary purification by ion exchange chromatography, and then to chromatography with S-Sepharose, and finally to affinity chromatography, thereby obtaining the present enzyme. In Example 1 shown below, enzyme specimen with activity $1.9 \times 10^3$ to $2.4 \times 10^3$ U/mg (assayed by the method for the measurement of enzymatic activity described below) was obtained by this type of procedure. This enzyme specimen was used for the determination of enzyme properties described below.

III. Method for the measurement of enzymatic activity

Z-Phe Leu Glu-pNA (wherein Z is a carbobenzoxy group and pNA is a p-nitroaniline group), used as a substrate, is dissolved in 50 mM Tris-HCl (pH 7.5, containing 2 mM calcium chloride and 2% DMF) so as to achieve a final substrate concentration of 0.2 mM. An enzyme solution is added to this mixture, and a reaction is conducted at 37° C. for 10 minutes, then the 410 nm absorbance of the p-nitroaniline released into the liquid by the enzymatic reaction is measured. The enzymatic activity present when this absorbance is 1.0 is defined as 1 unit (U).

IV. Enzyme properties

The enzymatic properties and protein chemical properties of BLase of the present invention are as follows.

(1) Enzymatic action and substrate specificity (i) The synthetic substrates shows in Table 1 were prepared, and each of them was dissolved in 50 ml Tris-HCl (pH 7.5, containing 2 mM calcium chloride and dimethylformamide (DMF) or dimethyl sulfoxide (DMSO) in the proportions indicated by Table 1) so as to achieve the concentration shown in Table 1. Then, the present enzyme was added to this solution and a reaction was conducted at 25° C. The 410 nm absorbance of the p-nitroaniline released into the liquid by the enzymatic reaction was measured, and the quantity (nmol) of p-nitroaniline released from 1 mg of the substrate per minute was calculated; the results so obtained are shown in Table 1.

TABLE 1

| Substrate | Final concentration of substrate (mM) | Concentration of DMF or DMSO (%) | | Released p-nitroaniline (nmol/mg/min.) |
| --- | --- | --- | --- | --- |
| Z Phe Leu Glu pNA* | 0.05 | DMF | 20 | 246.2 |
| Z Phe Leu Asp pNA* | 0.05 | DMF | 20 | 0.0 |
| Ac Glu pNA* | 2.0 | DMF | 10 | 90.0 |
| Ac Asp pNA* | 2.0 | DMF | 10 | 0.0 |
| Bz Tyr pNA* | 0.1 | DMF | 10 | 0.0 |
| Bz Arg pNA* | 0.4 | DMSO | 0.8 | 0.0 |
| Z Gly Ser pNA* | 1.0 | DMF | 10 | 0.0 |
| Suc Ala Ala Ala pNA* | 1.0 | — | — | 0.0 |
| Leu pNA* | 10.0 | DMF | 10 | 0.0 |

*pNA: p-Nitroanilide (ii) Oxidized insulin B chain was selected as a protein substrate, and the actions of the present enzyme and V8 protease derived from *Staphylococcus aureus* upon this substrate were compared by the following procedure. First, oxidized insulin B chain was dissolved in 50 mM ammonium bicarbonate (pH 7.8), the present enzyme or the aforesaid V8 protease was added so as to achieve an enzyme/substrate ratio of 1/100 (W/W), and a reaction was conducted over a prescribed period of time. The reaction mixture was then subjected to HPLC using a 4.6×250 mm column packed with Vydac Protein $C_4$ (300 angstroms), which was eluted under a 0–50% acetonitrile linear gradient in 0.1% TFA, raising the acetonitrile concentration by 1.67%/min. Peptide mapping revealed that, when either of the enzymes was used, the peptide bonds at the carboxyl termini of the glutamic acid residues were cleaved, and the products of enzymatic hydrolysis induced by the two enzymes were identical with each other.

Thus, the results of the aforesaid analyses (i) and (ii) demonstrated that the present enzyme cleaves peptide bonds at the carboxyl termini of glutamic acid residues, and is indeed a glutamic acid specific endopeptidase.

(2) Optimal pH and stable pH range

Z-Phe Leu Glu-pNA as a substrate was dissolved solved in 50 mM Tris-HCl containing 10% DMF and 2 mM calcium chloride. Then, the present enzyme was added to this mixture, a reaction was conducted for 15 minutes at 37° C., and the 410 nm absorbance of the p-nitroaniline released into the liquid by the enzymatic reaction was measured. The aforesaid reaction was conducted at various pH values, and the results revealed that the optimal pH for enzymatic activity is 8.0.

Next, the present enzyme was maintained at 25° C. for 24 hours at various pH values, and in each case the enzyme after this treatment was allowed to react with a substrate in accordance with the procedure described in the method for the measurement of enzymatic activity mentioned above. The results indicate that the stable pH range of the present enzyme is about 4.0–10.0. In a pH range of 6.5–8.5, the enzymatic activity is maintained at 100%, and in pH ranges exceeding 4.0 up to less than 6.5, and exceeding 8.5 up to 10.0, the enzymatic activity is maintained at 80–100%.

(3) Thermal stability

The present enzyme was maintained for 15 minutes at various temperatures in a buffer solution containing 2 mM calcium chloride at pH 7.8. In each case, the enzyme after this treatment was allowed to react with a substrate in accordance with the procedures described in the method for the measurement of enzymatic activity mentioned above. The results indicated that under the aforesaid conditions the present enzyme is stable at temperatures up to 60° C. When the present enzyme was similarly kept in solutions not containing calcium chloride, it was stable at temperatures up to 50° C.

(4) Effect of inhibitors

The present enzyme is completely inhibited by diisopropyl fluorophosphate (DFP). This fact indicates that the present enzyme is classified as a serine protease.

The present enzyme is also completely inhibited by Z-Phe Leu Glu $CH_2Cl$. This fact indicates that the present enzyme is a glutamic acid specific endopeptidase.

The present enzyme is partially inhibited by EDTA, with a maximum inhibition ratio of approximately 72%. This inhibitory effect of EDTA is completely nullified by the addition of metal ions at low concentrations ($10^{-4}$ to $10^{-3}$M of calcium or magnesium ions, etc.).

The aforesaid facts indicate that the present enzyme is a typical serine protease, the stability of which is related to the presence of metal ions.

(5) Molecular weight

The molecular weight of the present enzyme was determined by SDS-PAGE using 15% gel (1.0 mm) and Rainbow™ Protein Molecular Weight Marker (Amersham), and was calculated to be 26,000. The molecular weight was also calculated from the amino acid sequence determined on the basis of the gene sequencing analysis to be described below, and the value so obtained was 23,567 which is somewhat different from the aforesaid value obtained by SDS-PAGE. Nevertheless, the results of the various protein chemical analyses to be described below (amino acid composition, amino terminal sequences, amino acid composition in the vicinity of the carboxyl terminus) agreed well with the structure deduced from the DNA sequence. This indicates that the molecular weight obtained by SDS-PAGE was, in fact, slightly in excess of the true value.

(6) Isoelectric point

Investigation of the isoelectric point of the present enzyme using the Pharmacia FAST System (Pharmalite, pH 3.0–10.0) yielded values above pH 9.0, and a normal value could not be obtained.

(7) Amino acid composition

Using 4M methanesulfonic acid (containing 0.2% of 3-(2-aminoethyl)indole), the present enzyme was hydrolyzed at 110° C. for prescribed time intervals (24, 48, or 72 hours). The respective hydrolysates were then subjected to amino acid analysis using a Hitachi Model 835 amino acid analyzer. The results of this analysis, corrected for the decomposition of amino acids in the process of hydrolysis, are shown in Table 2. The amino acid composition calculated from the DNA sequence of the present enzyme (described below) are also shown for comparison in Table 2. The two sets of results clearly display good agreement.

TABLE 2

| Amino acid | Amino acid composition | |
|---|---|---|
| | Measured value (%) | Calculated value (%) |
| Asp | 8.38 | 8.10 |
| Thr | 11.68 | 12.61 |
| Ser | 13.49 | 14.41 |
| Glu | 5.48 | 4.95 |
| Pro | 4.79 | 4.50 |
| Gly | 13.61 | 13.06 |
| Ala | 5.24 | 5.41 |
| Cys/2 | 1.69 | 1.80 |
| Val | 6.08 | 5.86 |
| Met | 0.93 | 0.90 |
| Ile | 6.04 | 5.86 |
| Leu | 2.34 | 2.25 |
| Tyr | 7.97 | 7.66 |
| Phe | 2.38 | 2.25 |
| Lys | 2.70 | 2.70 |
| His | 1.73 | 1.80 |
| Arg | 4.11 | 4.05 |
| Trp | 1.37 | 1.80 |
| Total | 100.01 | 99.97 |

(8) Partial amino acid sequences (i) Amino acid sequence near N terminus

A Model 477A Protein Sequencer (Applied Biosystems) was used to analyze the amino acid sequence of the present enzyme in the vicinity of the amino terminus. The enzyme samples used were inhibited beforehand with DFP. The amino acid sequence from the amino terminus to the 23rd residue is shown in Table 3.

TABLE 3

| Degradation step | Amino acid | Recovery (%) |
| --- | --- | --- |
| 1 | Ser | 24.1 |
| 2 | Val | 85.6 |
| 3 | Ile | 81.6 |
| 4 | Gly | 90.2 |
| 5 | Ser | 22.8 |
| 6 | Asp | 51.7 |
| 7 | Asp | 73.1 |
| 8 | Arg | 61.3 |
| 9 | Thr | 39.8 |
| 10 | Arg | 55.6 |
| 11 | Val | 65.3 |
| 12 | Thr | 36.4 |
| 13 | Asn | 53.2 |
| 14 | Thr | 30.3 |
| 15 | Thr | 31.9 |
| 16 | Ala | 51.5 |
| 17 | Tyr | 62.3 |
| 18 | Pro | 42.7 |
| 19 | Tyr | 45.1 |
| 20 | Arg | 12.9 |
| 21 | Ala | 33.4 |
| 22 | Ile | 24.6 |
| 23 | Val | 22.7 |

(ii) Amino acid sequence near C terminus

Carboxypeptidase A (CPase A) or carboxypeptidase Y (CPase Y) was allowed to act upon samples of the present enzyme inhibited beforehand with DFP, and the quantities of amino acids released by these reactions were measured with an amino acid analyzer of Hitachi Model 835. However, the amino acid sequence in the vicinity of the carboxyl terminus of the present enzyme could not be accurately determined using either of the aforesaid carboxypeptidases. Nevertheless, the presence of glutamine, serine, alanine and asparagine in the vicinity of the carboxyl terminus was verified.

V. Determination of DNA sequence encoding BLase

Certain terminology employed in the specification of the present invention is defined as follows.

"Oligonucleotide" refers to a short single-strand DNA molecule. Oligonucleotides can be chemically synthesized in accordance with known methods. Unless otherwise stated, the oligonucleotides used in the processes of the present invention are chemically synthesized, and are purified by gel chromatography using Sephadex G50 and high-performance liquid chromatography (HPLC) with a reverse phase silica gel column.

"PCR" is an acronym of "polymerase chain reaction", and refers to a method for enzymatic amplification of a definite DNA region (Saiki et al., Science, 239, 487–497, 1988). First, the DNA to be amplified is converted to single-strand form by thermal denaturation, and oligonucleotide primers (two types, i.e., sense and antisense strands, each having a complementary sequence to the 3'-terminal region of the said single-stranded DNA) are annealed to the regions at the respective 3'-termini of the single-stranded DNA (i.e., the template DNA). Next, the extension of the DNA strands from the respective primers is accomplished by a reaction using DNA polymerase. By repeating this sequence of reactions, the target DNA can be amplified by a factor of 100,000 to 1,000,000.

"Southern blotting" is a method for determining whether or not a specified gene is contained in a DNA fragment obtained by cleavage with a certain restriction enzyme. Southern blotting is performed by first digesting the DNA sample under investigation with a restriction enzyme which specifically recognizes a certain base sequence in duplex DNA and cleaves this DNA at specific sites. The digest so obtained is subjected to 1% agarose gel electrophoresis, then denatured into single-stranded DNA by alkali treatment, and transferred to a nylon filter. Separately, an oligonucleotide or DNA fragment constituting a portion of the gene in question is prepared and labelled to obtain a probe. Hybridization of the single-stranded DNA on the nylon filter with this probe is then used to detect the presence of the gene in question.

"Ligation" refers to the creation of phosphodiester bond between two duplex DNA fragments. In this technique, in order to prevent the self-ligation of the duplex DNA fragments, one of the fragments is subjected to prior dephosphorylation treatment by the conventional method (T. Maniatis et al., "Molecular Cloning", 133–134, 1982). Ligation can be accomplished with T4 DNA ligase, using a well known type of buffer solution and reaction conditions.

"Transformation" refers to the phenomenon wherein the genotype of a cell (i.e., a host cell) is transformed by the introduction of exogenous genes (DNA) into the said cell. A cell which has undergone such a transformation is known as a "transformant", and is characterized by the capability for replication of the exogenous DNA either as a extranuclear component or in a form integrated into the chromosomes of the said cell.

Next, the method employed for the determination of the DNA sequence of BLase of the present invention will be described in the order of the processes involved. This DNA sequence was determined by the analysis of the genome DNA of the *Bacillus licheniformis* ATCC No. 14580 using a combination of PCR analysis, Southern blotting, direct sequencing techniques, etc.

(1) PCR analysis of genome DNA sequence

A DNA sequence encoding BLase can be obtained, for example, from genome DNA. In order to obtain the DNA, first, the genome DNA of *Bacillus licheniformis* ATCC No. 14580 is isolated from cultured cells of the said strain by the conventional technique (M. Stahl et al., J. Bacteriology, 154, 406–412, 1983). This genome DNA is used as the template DNA for PCR analysis. The oligonucleotide primers used for PCR are synthesized by conventional methods on the basis of the amino acid sequence in the vicinity of the amino terminus of the purified enzyme, determined in Section IV Item (8) above, and/or the amino acid sequences of the peptides obtained by partial hydrolysis of the said enzyme. For example, the oligonucleotide encoding the amino acid sequence Thr Asn Thr Thr Ala Tyr Pro Tyr which corresponds to the 12th through 19th positions reckoned from the amino terminus of BLase (see Table 3) is used as sense primer BL8 (shown by SEQ ID NO: 2). This oligonucleotide is a tricosamer which encodes the amino acid sequence up to the second base of the triplet codon for the tyrosine residue of c-terminus.

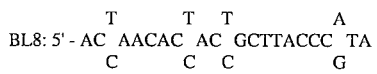

```
               T    T  T        A
BL8: 5'- AC  AACAC  AC  GCTTACCC  TA
          C      C   C          G
```

Separately, another oligonucleotide primer is synthesized on the basis of a peptide which is obtained by the decomposition of the purified enzyme with lysylendopeptidase followed by sequencing and the sequence of which is most reliable. As described in Example 2 below, the sequence Gly Tyr Pro Gly Asp Lys (SEQ ID NO: 8) is obtained, hence, the octadecamer complementary to an oligonucleotide encoding this amino acid sequence is used as antisense primer BL83 (shown by SEQ ID NO: 3).

```
          T A T C     T
BL83: 5'- TT TC CC GGATA CC
          C G  G A     G
```

Then, PCR is performed using the aforesaid genome DNA, the sense primer BL8, and the antisense primer BL83, thereby extending and amplifying the target DNA strands in the genome DNA. The PCR products so obtained are subjected to agarose gel electrophoresis, thereby obtaining a DNA fragment of approximately 370 bp. This DNA fragment is incorporated into a suitable vector, and after subcloning, the base sequence of the fragment is determined by the Sanger technique. The aforesaid amino acid sequence Gly Tyr Pro Gly Asp Lys which constituted the basis for the preparation of the anti-sense primer BL83 was identified as that located in positions 131–136 in the amino acid sequence of BLase.

(2) Southern blotting analysis of genome DNA

The genome DNA derived from the *Bacillus licheniformis* ATCC No. 14580, prepared in Item (1) above, is digested with the restriction enzyme SalI, and after separation by agarose gel electrophoresis, the DNA fragments so obtained are blotted onto a nylon membrane filter, and analyzed by the Southern technique. The probe used for hybridization is the BL8-BL83 PCR product obtained in Item (1) above, labelled with $^{32}$P-dCTP by the conventional method. The DNA fragment which displays positive hybridization to this BL8-BL83 product is recognized as a band corresponding to a length of approximately 3.1 kb.

(3) Sequencing of genome DNA by PCR

The genome DNA of the *Bacillus licheniformis* ATCC No. 14580, obtained in Item (1) above, is digested with SalI, then this digest is incorporated into a suitable vector, for example, pUC119 vector, and a PCR is conducted using a portion of the known DNA sequence as a primer. For example, a portion of the DNA sequence of pUC119 located upstream to the aforesaid genome DNA is used as sense primer RV (shown by SEQ ID NO: 4), and a DNA sequence complementary to a sequence in the vicinity of the 3' terminus of the 375 bp DNA fragment analyzed in Item (2) above is used as anti-sense primer B125 (shown by SEQ ID NO: 5).

RV: 5'-CAGGAAACAGCTATGAC

B125: 5'-TGTCCCAACAAGTGATGA

A DNA fragment of approximately 1050 bp is obtained by the PCR. The base sequence of this fragment can be determined by the direct DNA sequencing method (Gibbs et al., Pro. Natl. Acad. Sci. U.S.A., 86, 1919–1923, 1989). In this manner, the DNA sequence encoding BLase can be ascertained from the amino terminus up to the middle portion of the sequence.

Next, the portion of the sequence on the 3' side of the genome DNA can be determined by the following procedure. First, in the same manner as indicated above, the genome DNA of *Bacillus licheniformis* ATCC No. 14580 is digested with SalI, and a fragment of approximately 3.1 kb is isolated. This is inserted into M13mp11, and a PCR is conducted. The primers used for this PCR are partial fragments of the 375 bp DNA fragment analyzed in Item (2) above; one is sense primer B40 (shown by SEQ ID NO: 6) which is located upstream to the aforesaid antisense primer B125, and the other is antisense primer M4 (shown by SEQ ID NO: 7) which has a DNA sequence complementary to a portion of the DNA sequence of M13mp11, and is located downstream to the genome DNA.

B40: 5'- AAAACCGTCGCAACAGCC
M4: 5'- GTTTTCCCAGTCACGAC

The aforesaid PCR yields a DNA fragment of approximately 2.2 kb. The base sequence of this DNA fragment can be determined by the direct DNA sequencing method. In this manner, the base sequence from the 3' terminus to the middle portion of the genome DNA is determined.

The complete DNA sequence of BLase determined in this manner as well as the amino acid sequence determined from this DNA sequence are shown in SEQ ID NO: 1 and FIG. 1. From SEQ ID NO: 1 and FIG. 1, it is recognized that the gene encoding the mature protein derived from *Bacillus licheniformis* contains a DNA sequence encoding a signal peptide composed of the 94 amino acid residues from N-formylmethionione residue in the −94 position to the lysine residue in the −1 position, and a DNA sequence encoding the mature protein composed of the 222 amino acid residues from the serine residue in the +1 position to the glutamine residue at the +222 position. Ordinarily, ATG codes for methionine, but in this case TTG (fMet) appears to be the translation start codon. In the 332 bp segment of the 5' untranslated region starting from the SalI cleavage site, there are a promoter region containing a −35 sequence, a Pribnow box, and a Shine-Dalgarno sequence which is present 9 bases upstream from the aforesaid inferred translation start codon TTG. In the 3' untranslated region, an inverted complementary repeat composed of 13 base pairs is located 8 bases downstream from the stop codon TAA.

VI. Construction of expression vectors

Figure 3:
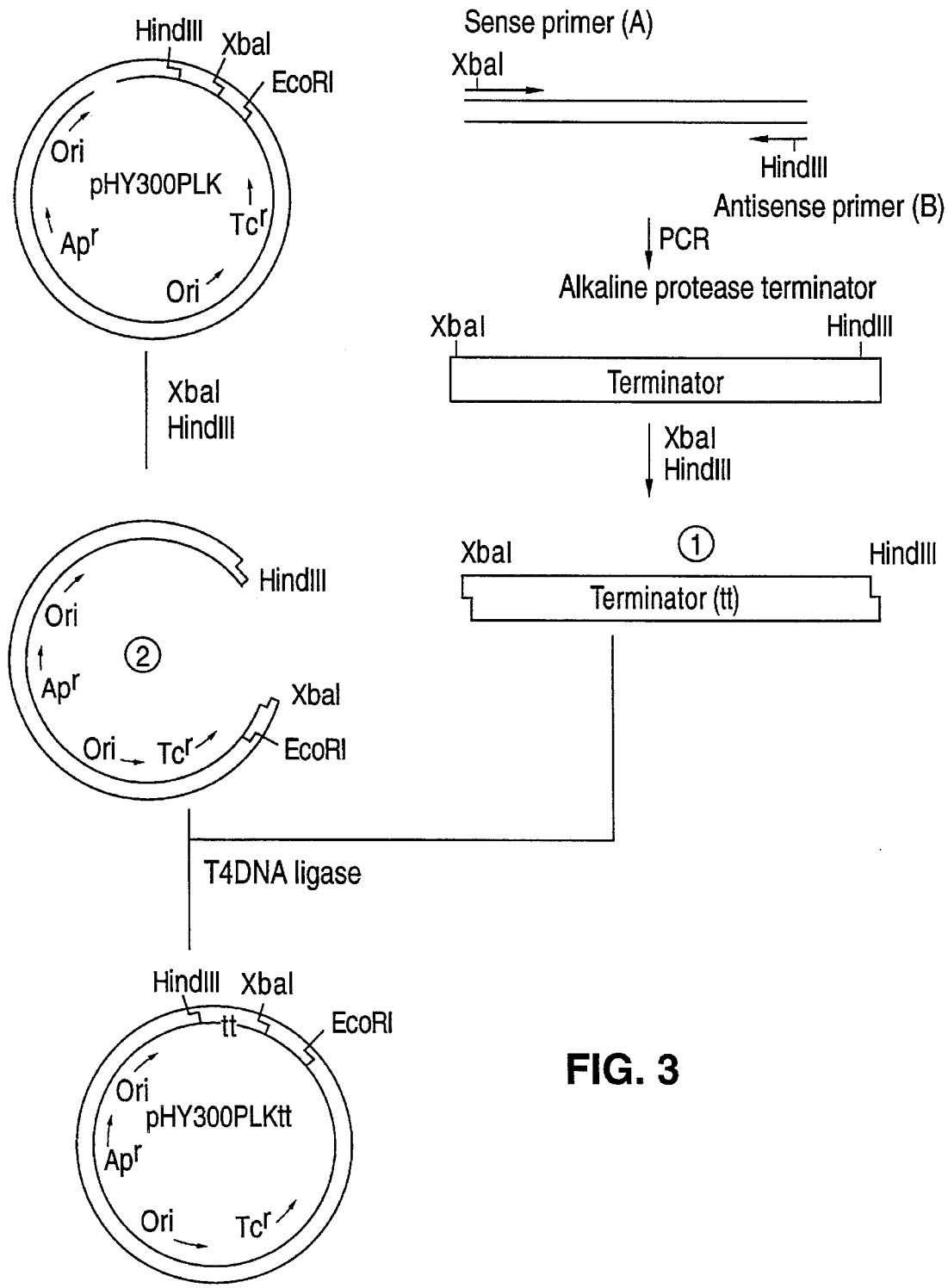

As shown in FIG. 2, pHY300BLtt, an example of the expression vectors of the present invention, is obtained from the shuttle vector pHY300PLKtt, which contains an alkaline protease terminator derived from *Bacillus subtilis* ATCC No. 6051, by inserting a DNA fragment encoding BLase of the present invention shown in SEQ ID NO: 1 (i.e., a DNA fragment containing a promoter, a DNA sequence encoding a signal peptide, a DNA sequence encoding the mature peptide of BLase, and a terminator) into the said vector pHY300PLKtt. As shown in FIG. 3, the aforesaid vector pHY300PLKtt is obtained from a vector pHY300PLK which is a shuttle vector of *E. coli* and *B. subtilis*, by inserting an alkaline protease terminator derived from *Bacillus subtilis* ATCC No. 6051 into the vector pHY300PLK.

The aforesaid procedure will now be further explained in the order of the processes involved. First, as shown in FIG. 3, genome DNA is isolated from the *Bacillus subtilis* ATCC No. 6051 by the method of M. Stahl et al. (supra.), and this is employed as template DNA. Next, a fragment composed of a DNA sequence corresponding to the vicinity of the 5' terminus of the terminator portion of the alkaline protease gene derived from the *Bacillus subtilis* I-168, with an added XbaI cleavage site, and a fragment complementary to a DNA sequence corresponding to the vicinity of the 3' terminus of the terminator portion, with an added HindIII cleavage site, are synthesized chemically, and a PCR is conducted using these fragments as primers. The DNA fragment so obtained is then cleaved with XbaI and HindIII, thereby obtaining a fragment (1) shown in FIG. 3. Next, pHY300PLK is cleaved with XbaI and HindIII, thereby obtaining the larger fragment (2) shown in FIG. 3. The shuttle vector pHY300PLKtt, containing the alkaline protease terminator derived from *Bacillus subtilis* ATCC No. 6051, is then constructed by the ligation of these fragments (1) and (2).

Next, genome DNA is isolated from cultured cells derived from *Bacillus licheniformis* ATCC No. 14580 and used as template DNA. Then, a fragment composed of a DNA sequence corresponding to the vicinity of the 5' terminus of this template DNA with an added EcoRI cleavage site and a fragment complementary to the DNA sequence corresponding to the 3' terminus of the template DNA with an added XbaI cleavage site are synthesized and used as the sense and antisense primers, respectively. A PCR is conducted using the aforesaid template DNA, sense primer, and antisense primer. Then, the fragment so obtained is cleaved with EcoRI and XbaI, thereby obtaining a DNA fragment (3) encoding BLase (see FIG. 2). This fragment (3) contains a promoter, a DNA sequence encoding a signal peptide, a DNA sequence encoding mature BLase, and a terminator. Next, the aforesaid vector pHY300PLKtt is cleaved with EcoRI and XbaI, thereby obtaining the larger fragment (4). The expression vector pHY300BLtt of the present invention is then obtained by ligating the aforesaid fragments (3) and (4) (see FIG. 2).

This expression vector pHY300BLtt contains, under the control of the BLase promoter, a DNA sequence encoding the signal peptide from the N-formylmethionine residue in the −94 position to the lysine residue in the −1 position; a DNA sequence encoding a mature peptide extending from the serine residue in the +1 position to the glutamine residue in the +222 position of BLase; and a 3' untranslated region comprising a terminator. Still further downstream, the terminator of the alkaline protease derived from *Bacillus subtilis* ATCC No. 6051 is present.

VII. Preparation of transformants and production of BLase

The expression vector obtained in Section VI above is introduced into suitable host cells by a conventional method. For example, the aforesaid vector pHY300BLtt can be introduced into *Bacillus subtilis* ISW1214 (Takara Shuzo) by the method of J. Spiezen et al. (Proc. Natl. Acad. Sci. U.S.A. 44, 1072, 1958). The transformant (*Bacillus subtilis* pHY300BLtt/ISW1214) is cultivated in any medium suitable for the host, thereby producing BLase of the present invention. Finally, BLase is isolated from the culture broth wherein the transformant has been grown and purified by the process described in Section II above.

EXAMPLES

The present invention will now be further explained with reference to the specific examples.

Example 1

*Bacillus licheniformis* ATCC No. 14580 was cultivated at 28° C. for 36 hours in a medium of pH 7.0 containing 2.0% of glucose, 2.0% of soybean meal, 0.25% of corn steep liquor, 0.5% of ammonium sulfate, 0.05% of dipotassium hydrogen phosphate, 0.05% of magnesium sulfate heptahydrate, 0.01% of ferrous sulfate heptahydrate, and 0.3% of calcium carbonate. Ninety five liters of the culture broth were filter pressed, and concentrated to approximately 14 liters by means of an ultrafiltration module (Nitto Ultrafiltration Module NTU 2020T P18B (HF); cutoff MW 20,000) and a centrifuge (4200 rpm, 30 minutes). This concentrated cell-free broth was diluted to approximately 28 liters (1.90 ms/cm) with 2 mM calcium chloride. Then the pH of the diluted cell-free broth was adjusted to 6.0 by addition of hydrochloric acid. To this was added approximately 4 liters of Amberlite CG-50 which had been equilibrated with a 10 mM acetate buffer (pH 6.0) containing 2 mM calcium chloride, and the mixture was agitated for 4 hours at room temperature. After verifying that the supernatant had no BLase activity, the supernatant was discarded. Then the Amberlite CG-50 was packed into a 14×32 cm glass column. After washing with approximately 10 liters of 10 mM acetate buffer (pH 6.0) containing 2 mM calcium chloride, elution was performed with 0.5M sodium acetate buffer (pH 8.5) also containing 2 mM calcium chloride.

The fractions having BLase activity eluted from the Amberlite CG-50 were combined (the total volume of the fractions was 2.7 liters) and dialyzed against water for 48 hours. The dialyzate was diluted to 8 liters (2.23 ms/cm) with 2 mM calcium chloride, and after adjustment to pH 6.0, the fluid was adsorbed onto approximately 800 ml of S-Sepharose, packed in a 5×40 cm column, which had been equilibrated beforehand with a 5 mM acetate buffer solution (pH 6.0) containing 2 mM calcium chloride. After washing with approximately 5.liters of buffer solution with the same composition as that used for the above-mentioned equilibration, the column was subjected to elution with 7 liters of this buffer solution under a linear gradient of 0–0.2M sodium chloride. The fractions having BLase activity were combined (the total volume of the fractions was 900 ml), and dialyzed overnight against a 2 mM aqueous solution of calcium chloride, thereby obtaining approximately 950 ml of dialyzate (0.86 ms/cm). The pH of this dialyzate was adjusted to 7.5, then promptly subjected to affinity chromatography. The carrier used in this affinity chromatography process was approximately 340 ml of CH Sepharose 4B (Phe Leu-D-GluOMe) packed into a 3×48 cm column, and equilibrated with 5 mM Tris-HCl (pH 7.5) containing 2 mM calcium chloride. After adsorbing the aforesaid dialyzate in this column, the column was washed with approximately 5 liters of buffer solution with the same composition as that used for equilibration of the column, and then subjected to elution with 3.5 liters of the buffer solution of the same composition under a linear gradient of 0–0.7M sodium chloride.

The BLase activity of each fraction so obtained was measured by the method for the measurement of enzymatic activity shown in Section III of Description of the preferred Embodiments. The results are shown in FIG. 4. The 280 nm absorbance of each fraction was measured as an index of protein concentration, and the results so obtained are also shown in FIG. 4. This figure shows that the BLase was eluted at a concentration of approximately 0.5M of sodium chloride. The BLase so obtained displayed a single band in SDS-PAGE. In this manner, an 833.1 mg specimen of the said enzyme (quantitated with a Bio Rad protein assay kit), with specific activity of $1.9 \times 10^3 – 2 \times 10^3$ U/mg, was obtained from 95 liters of the culture broth. The yield of the enzymatic activity was 27.5%.

Example 2

Determination of base sequence of DNA encoding BLase
(1) PCR analysis of internal base sequence of genome DNA One hundred micrograms of the purified BLase obtained in Example 1 which had been treated with DFP was added in 150 μl of 0.05M Tris-HCl (pH 9.0) containing 1M urea, and digested with 1 μg of lysyl endopeptidase (Wako Pure Chemical Industries, Ltd.) at 37° C. for 5 hours. The resulting enzyme digest was then isolated and purified by high-performance liquid chromatography using a column packed with TSKgel ODS-120T (4.6×250 mm, Tosoh Co. Ltd.) The amino acid sequences of the digested fragments so obtained were investigated with a Model 477A Protein Sequencer (Applied Biosystems), thereby determining the amino acid sequences of five types of fragments. Three of these sequences are indicated below as well as in SEQ ID NOS: 8, 9, and 10.

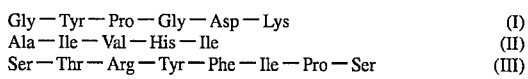

Next, genome DNA was isolated from *Bacillus licheniformis* ATCC No. 14580 by the method of M. Stahl et al. (supra.), and the DNA was used as a template for PCR analysis. The oligonucleotide primers used for the PCR were prepared on the basis of known portions of the amino acid sequence of the BLase produced by *Bacillus licheniformis* ATCC No. 14580. First, an oligonucleotide encoding the amino acid sequence beginning with the 12th position and terminating with the 19th position from the amino terminus of the BLase molecule (see Table 3), that is, Thr Asn Thr Thr Ala Tyr Pro Tyr (except that the said oligonucleotide only extends through the second base of the triplet coding for the tyrosine residue at the carboxyl terminal of the oligopeptide, i.e., the said oligonucleotide is a tricosamer) was synthesized chemically. This was used as sense primer BL8 (shown by SEQ ID NO: 2).

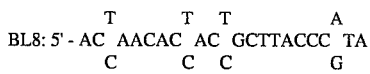

Next, an octadecamer complimentary to the DNA sequence encoding an amino acid fragment which is a product obtained in the aforesaid lysyl endopeptidase digestion and which has an amino acid sequence with the greatest degree of reliability [i.e., Gly Tyr Pro Gly Asp Lys (shown by SEQ ID NO: 8] was synthesized chemically. This was used as antisense primer BL83 (shown by SEQ ID NO: 3).

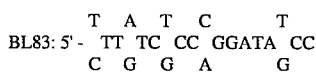

Using the aforesaid template DNA and oligonucleotide primers, the DNA was amplified by the PCR method (Saiki et al., Science 239, 487–491, 1989 ). A portion of the amplified products were analyzed by 1% agarose gel electrophoresis, thereby confirming the presence of an approximately 370 bp DNA fragment. This fragment was isolated and, after blunting the ends with Klenow fragment, the fragment was cloned in M13mp11 which had been digested with SmaI, and the DNA sequence of the fragment was determined by the Sanger method (Sanger et al., Proc. Natl. Acad. Sci. U.S.A., 74, 5463–5467, 1977). In this manner, the base sequence of a 375 bp fragment was determined, and the amino acid sequence corresponding to BL83 was found to be located at positions 131 through 136. Furthermore, the aforesaid amino acid sequences (II) and (III) were found to be located at positions 21 through 25 and 79 through 86, respectively.

(2) Southern blotting analysis of genome DNA

The genome DNA derived from *Bacillus licheniformis* ATCC No. 14580 obtained by the procedure described in Item (1) above was digested with the restriction enzyme SalI, and after separation of the products by 1% agarose gel electrophoresis, the DNA fragments were blotted onto a nylon membrane filter and analyzed by the Southern technique. The probe used for the hybridization was the BL8-BL83 PCR product obtained in Item (1) above, and labelled with $^{32}$P-dCTP by the conventional method. The DNA fragment which displayed positive hybridization to this BL8-BL83 product was recognized as a band corresponding to a length of approximately 3.1 kb.

(3) Determination of genome DNA sequence by PCR

The genome DNA of *Bacillus licheniformis* ATCC No. 14580, obtained in Item (1) above, was digested with SalI, then the ends of the fragments were blunted with T4 DNA polymerase. This blunt-end fragment was ligated with a dephosphorylated SmaI-digested pUC119 vector. This ligation reaction was performed with a commercial kit (Takara Shuzo).

Next, the sense primer RV (shown by SEQ ID NO: 4) and the antisense primer B125 (shown by SEQ ID NO: 5), with the base sequences also indicated below, were synthesized chemically and added to an aliquot of the reaction mixture for the aforesaid ligation reaction, allowing a PCR reaction to be carried out.

The sense primer RV is a portion of the DNA sequence of pUC119 and is located upstream to the aforesaid genome DNA, while the antisense primer B125 is a DNA sequence complementary to a sequence in the vicinity of the 3' terminus of the 375 bp DNA fragment analyzed in Item (2) above.

A DNA fragment of approximately 1050 bp was obtained by the aforesaid PCR. The base sequence of this fragment was determined by the direct DNA sequencing method (Gibbs et al., Pro. Natl. Acad. Sci. U.S.A., 86, 1919–1923, 1989). In this manner, the DNA sequence encoding the present enzyme was ascertained from the 5' terminus up to the middle portion of the sequence.

The genome DNA of the *Bacillus licheniformis* ATCC No. 14580, obtained in Item (1) above, was digested with SalI and subjected to 1% agarose gel electrophoresis, thereby isolating an approximately 3.1 kb fragment. This fragment was blunt ended with Klenow fragment, and was ligated with dephosphorylated SmaI-digested fragments of M13mp11. Using this as a template, a PCR was conducted. The primers used for this PCR were sense primer B40 (shown by SEQ ID NO: 6) which is a portion of the 375 bp DNA fragment analyzed in Item (2) above (upstream to the aforesaid primer B125), and antisense primer M4 (shown by SEQ ID NO: 7) which is a DNA sequence complementary to a portion of the DNA sequence of M13mp11 located downstream to the genome DNA.

The aforesaid PCR yielded an approximately 2.2 kb DNA fragment. The base sequence of this DNA fragment was determined by the direct DNA sequencing method. In this manner, the base sequence from the 3' end to the middle portion of the genome DNA was determined.

The complete DNA sequence of BLase determined in this manner as well as the amino acid sequence deduced from the DNA sequence are shown by SEQ ID NO: 1 and FIGS. 1—1 to 1-3.

The DNA sequence of BLase, as well as DNA sequences which hybridize to the said DNA sequence are also useful for producing a protease with BLase activity which is also within the scope of the present invention. The DNA sequence which hybridizes to the DNA sequence of BLase can be obtained, for example, by the following process.

Various DNA fragments, for example, DNA fragments derived from various organisms are screened by the use of whole or a part of the DNA sequence of BLase, e.g. a 1124 bp DNA fragment which is from A in the 248 position to T in the 1371 position of SEQ ID NO:1, as a probe. For example, the Southern hybridization technique (Southern, E. M., J. Mol. Biol. 98, 503–517, 1975) is employed by the use of the $^{32}$p-labelled probe, and a hybridization buffer having the following composition.

| | |
|---|---|
| 0.5 M | NaH$_2$PO$_4$ (pH 7.2) |
| 1 mM | EDTA |
| 1% | BSA |
| 7% | SDS |

After the hybridization is carried out at 65° C. overnight, a filter, to which the probe has been hybridized, is washed 4 times at room temperature with 2×SSC, 0.1% SDS, four times each wash being carried out for 10 minutes, at room temperature, thus obtaining a DNA fragment which has about 65% homology with the DNA sequence of BLase. When the filter is washed once for 20 minutes at 50° C., a DNA fragment which has about 80% homology with the DNA sequence of BLase can be obtained.

(4) Construction of expression vector (4)-1 Construction of shuttle vector pHY300PLKtt A genome DNA was isolated from *Bacillus subtilis* ATCC No. 6051 by the method of M. Stahl et al. (supra.), and this was employed as a template DNA. Next, as primers, a fragment composed of a DNA sequence corresponding to the vicinity of the 5' terminus of the terminator portion of an alkaline protease gene derived from *Bacillus subtilis* 1–168 (Journal of Bacteriology 158, 411–418, 1984), with an added XbaI cleavage site (sense primer A, shown by SEQ ID NO: 11), and a fragment complementary to a DNA sequence corresponding to the vicinity of the 3' terminus of the terminator portion, with an added HindIII cleavage site (antisense primer B, shown by SEQ ID NO: 12), were synthesized chemically.

Sense primer A:
5' - GAGTCTAGAGCAGCTGCACAATAATAG - 3'
Antisense primer B:
5' - GAGAAGCTTGACAGAGAACAGAGAAG - 3'

Then, a PCR was conducted using the aforesaid template DNA and these two primers. The DNA fragment so obtained was then cleaved with XbaI and HindIII, thereby obtaining fragment (1) shown in FIG. 3. Next, the shuttle vector pHY300PLK (Takara Shuzo) was cleaved with XbaI and HindIII, thereby obtaining the larger fragment (2) (see FIG. 3). A shuttle vector pHY300PLKtt, containing the alkaline protease terminator derived from *Bacillus subtilis* ATCC No. 6051, was then constructed by ligation of these fragments (1) and (2).

(4)-2 Construction of expression vector pHY300BLtt

A genome DNA was isolated from cultured cells of *Bacillus licheniformis* ATCC No. 14580 by the method of M. Stahl et al. (supra.) and used as a template DNA. Then, a single-stranded DNA fragment corresponding to the vicinity of the 5' terminus of this template DNA with an added EcoRI cleavage site and a single-stranded DNA fragment complementary to a DNA sequence corresponding to the 3' terminus of the template DNA with an added XbaI cleavage site were synthesized and used as sense primer C (shown by SEQ ID NO: 13) and antisense primer D (shown by SEQ ID NO: 14), respectively.

Sense primer C:
5' - CAAGAATTCGGCTTCCCGTGCGCCTCC - 3'
Antisense primer D:
5' - TTGTCTAGAATTTGCCGATCAGCGGTC - 3'

A PCR was conducted using the aforesaid template DNA, sense primer C, and antisense primer D. Then, the fragment so obtained was cleaved with EcoRI and XbaI, thereby obtaining a DNA fragment (3) encoding BLase (see FIG. 2). Next, the aforesaid vector pHY300PLKtt was cleaved with EcoRI and XbaI, thereby obtaining the larger fragment (4). The aforesaid fragments (3) and (4) were then ligated with T4 DNA ligase. The ligation mixture was used to transform *E. coli* K-12 C600. The transformants were cultivated on an agar plate medium containing ampicillin, and the ampillicin-resistant colonies were selected. Then, plasmid DNA was isolated from the cells of the selected colonies, and the insertion of the aforesaid DNA fragment (3) in the correct direction was verified from restriction enzyme cleavage patterns.

(5) Preparation of transformants and production of BLase

The expression vector pHY300BLtt obtained in Item (4) above was introduced into *Bacillus subtilis* ISW1214 (Takara Shuzo) by the method of J. Spizien et al. (Proc. Natl. Acad. Sci. U.S.A. 44, 1072 (1958)). The bacteria were then cultivated on a plated agar medium containing tetracycline, and the tetracycline-resistant colonies were selected, thus obtaining the desired transformant (*Bacillus subtilis* pHY300BLtt/ISW1214).

The transformant was transplanted to 5 ml of LB medium (10 g trypton, 5 g yeast extract, and 5 g sodium chloride with water added to yield a total volume of 1 liter; pH 7.2) and shake-cultured at 37° C. for 18 hours. Then, 1 ml of this culture broth was added to 10 ml of Sc$^+$ medium which had been sterilized in an autoclave at 120° C. for 20 minutes, and shake-cultured was carried out at 28° C.

| Composition of Sc$^+$medium | |
|---|---|
| Soluble starch | 10 g |
| Glycerol | 5 g |
| Bacto soytone | 5 g |
| CSL | 2.5 g |
| Yeast extract | 1 g |
| Calcium carbonate | 3 g |

Water is added so that the total volume should be 1 L (pH 7.0)

The aforesaid culture broth was centrifuged at 2500×g for 5 minutes, and the supernatant was obtained. The BLase activity of this supernatant was measured by the method for the measurement of enzymatic activity described in the Description of the Preferred Embodiments. The results of these measurements are shown in Table 4. The quantity of protein per liter of the culture broth was calculated on the basis of an assumed BLase specific activity of 2500 U/mg.

TABLE 4

| Cultivation period (days) | BLase activity (units/ml) | Protein content (mg/L) |
|---|---|---|
| 1 | 15 | 6.0 |
| 2 | 56 | 22.4 |
| 3 | 72 | 28.8 |

TABLE 4-continued

| Cultivation period (days) | BLase activity (units/ml) | Protein content (mg/L) |
|---|---|---|
| 4 | 79 | 31.6 |
| 5 | 69 | 27.6 |

As described above, the present invention provides a new protease which specifically cleaves the peptide bonds at the carboxyl termini of glutamic acid residues in the amino acid sequences of polypeptides, a method for the preparation of the protease from bacteria of genus Bacillus, a DNA sequence encoding the protease, an expression vector containing the DNA sequence, a transformant obtained by introduction of the expression vector into a host, and a method for the production of the protease using the transformant. This type of protease can be utilized for a variety of purposes, such as protein analysis and cleavage of the peptide chains of fusion proteins at desired sites, etc.

The following specific sequence information and descriptions are provided in order to comply with the formal requirements of the submission of sequence data to the United States Patent and Trademark Office and are not intended to limit the scope of what the inventors regard as their invention. Variations in sequences which will become apparent to those skilled in the art upon review of this disclosure and which are encompassed by the attached claims are intended to be within the scope of the present invention. Further, it should be noted that efforts have been made to insure accuracy with respect to the specific sequences and characteristic description information describing such sequences, but some experimental error and/or deviation should be accounted for.

What is claimed is:

1. A purified and isolated DNA sequence which encodes a protease which contains an amino acid sequence from serine in the +1 position to glutamine in the +222 position of SEQ ID NO: 1.

2. A purified and isolated DNA sequence which encodes a protease which contains an amino acid sequence from serine in the +1 position to glutamine in the +222 position of SEQ ID NO: 1, and cleaves the peptide bonds at the carboxyl termini of glutamic acid residues in polypeptides.

3. A DNA sequence of claim 2, which DNA sequence contains a base sequence from the thymine residue in the 605 position to the adenosine residue in the 1270 position of SEQ ID NO: 1.

4. A DNA sequence of claim 1, which encodes a protease containing an amino acid sequence from N-for-mylmethionine at the −94 position to the glutamine at the +222 position of SEQ ID NO: 1.

5. A DNA sequence of claim 4, which contains a base sequence, from the thymine residue in the 323 position to the adenosine residue in the 1270 position, of SEQ ID NO: 1.

6. An expression vector containing a DNA sequence of claim 1.

7. An expression vector of claim 6, which is expressed in bacteria of the genus bacillus.

8. A transformant obtained by introducing the expression vector of claim 6 into a host.

9. A transformant of claim 8, wherein said host is a strain belonging to the genus Bacillus.

10. A DNA sequence of claim 2, which is derived from *Bacillus licheniformis*.

11. A DNA sequence of claim 10, which is derived from *Bacillus licheniformis* ATCC No. 14580.

* * * * *

UNITED STATES PATENT AND TRADEMARK OFFICE
CERTIFICATE OF CORRECTION

PATENT NO. : 5,459,064
DATED : October 17, 1995
INVENTOR(S) : Hiroshi Teraoka, et. al.

It is certified that error appears in the above-indentified patent and that said Letters Patent is hereby corrected as shown below:

Title page, item [54] and col. 1, line 1, Title should read--DNA ENDCODING A BACILLUS LICHENIFORMIS PROTEASE--.

Column 27, Line 1 (in Claim 4)
"N-for mylmethionine"

Should be:
--N-formylmethionine--

Column 27, Line 10 (in Claim 4)
"genus bacillus"

Should be:
--genus Bacillus--

Signed and Sealed this

Ninth Day of April, 1996

Attest:

BRUCE LEHMAN

*Attesting Officer*  Commissioner of Patents and Trademarks

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1448 base pairs
        ( B ) TYPE: nucleic acid
        ( C ) STRANDEDNESS: double
        ( D ) TOPOLOGY: linear ( i i ) MOLECULE TYPE: genomic DNA ( v i ) ORIGINAL SOURCE:
        ( A ) ORGANISM: Bacillus licheniformis
        ( B ) STRAIN: ATCC NO. 14580

( i x ) FEATURE:
        ( A ) NAME/KEY: coding sequence
        ( B ) LOCATION: 323 to 1270
        ( C ) IDENTIFICATION METHOD: by experiment
        ( A ) NAME/KEY: signal peptide
        ( B ) LOCATION: 323 to 604
        ( C ) IDENTIFICATION METHOD: by experiment
        ( A ) NAME/KEY: mature peptide
        ( B ) LOCATION: 605 to 1270
        ( C ) IDENTIFICATION METHOD: by experiment
        ( D ) OTHER INFORMATION:
            $X_{aa}$ at −94 position of amino acid
            sequence: formyl methionine ( x i ) SEQUENCE DESCRIPTION: SEQ ID NO:1:

```
TCGACGGCTT  CCCGTGCGCC  TCCGGGATCG  CTGTGATAAT  TGACAACCAC  ATTCATCTTT      60

TCTTTTCCAA  ACCGTTCTGC  AACCGCTTG   CCTATACCTT  TTGAAGAGCC  GGTCACAATT     120

GCTGTTTTTC  CTTTTAAATC  ACTATACAAC  CTAAACACCC  CTCAATTTCT  TTTCTCCATG     180

TACATTACCC  GGTATCAATA  TATGATCAAA  CAAAATGTTA  ATACACACCT  TTAGTATGAT     240

CTTTTTTAAA  CATATGGAAA  ATTCAGAATT  ATTTTGTTAA  TATCTAACTT  GTACTTACAA     300

CAAAATAAGG  AAGTGATATG  AT  TTG  GTT  AGT  AAA  AAG  AGT  GTT  AAA  CGA  GGT   352
                            Xaa Val Ser Lys Lys Ser Val Lys Arg Gly
                            −94          −90                      −95

TTG  ATC  ACA  GGT  CTC  ATT  GGT  ATT  TCT  ATT  TAT  TCT  TTA  GGT  ATG  CAC   400
Leu  Ile  Thr  Gly  Leu  Ile  Gly  Ile  Ser  Ile  Tyr  Ser  Leu  Gly  Met  His
                −90               −85                       −80
```

```
CCG GCC CAA GCC GCG CCA TCG CCT CAT ACT CCT GTT TCA AGC GAT CCT        448
Pro Ala Gln Ala Ala Pro Ser Pro His Thr Pro Val Ser Ser Asp Pro
        -75             -70                     -65

TCA TAC AAA GCG GAA ACA TCG GTT ACT TAT GAC CCA AAC ATT AAG AGC        496
Ser Tyr Lys Ala Glu Thr Ser Val Thr Tyr Asp Pro Asn Ile Lys Ser
        -60             -55                     -50

GAT CAA TAC GGC TTG TAT TCA AAA GCG TTT ACA GGC ACC GGC AAA GTG        544
Asp Gln Tyr Gly Leu Tyr Ser Lys Ala Phe Thr Gly Thr Gly Lys Val
        -45             -40                     -35

AAT GAA ACA AAG GAA AAA GCG GAA AAA AAG TCA CCC GCC AAA GCT CCT        592
Asn Glu Thr Lys Glu Lys Ala Glu Lys Lys Ser Pro Ala Lys Ala Pro
-30             -25                     -20                     -15

TAC AGC ATT AAA TCG GTG ATT GGT TCT GAT GAT CGG ACA AGG GTC ACC        640
Tyr Ser Ile Lys Ser Val Ile Gly Ser Asp Asp Arg Thr Arg Val Thr
        -1  1                   5                       10

AAC ACA ACC GCA TAT CCG TAC AGA GCG ATC GTT CAT ATT TCA AGC AGC        688
Asn Thr Thr Ala Tyr Pro Tyr Arg Ala Ile Val His Ile Ser Ser Ser
        15              20                      25

ATC GGT TCA TGC ACC GGA TGG ATG ATC GGT CCG AAA ACC GTC GCA ACA        736
Ile Gly Ser Cys Thr Gly Trp Met Ile Gly Pro Lys Thr Val Ala Thr
        30              35                      40

GCC GGA CAC TGC ATC TAT GAC ACA TCA AGC GGT TCA TTT GCC GGT ACA        784
Ala Gly His Cys Ile Tyr Asp Thr Ser Ser Gly Ser Phe Ala Gly Thr
45              50                      55                      60

GCC ACT GTT TCG CCG GGA CGG AAC GGG ACA AGC TAT CCT TAC GGC TCA        832
Ala Thr Val Ser Pro Gly Arg Asn Gly Thr Ser Tyr Pro Tyr Gly Ser
                65                      70                      75

GTT AAA TCG ACG CGC TAC TTT ATT CCG TCA GGA TGG AGA AGC GGA AAC        880
Val Lys Ser Thr Arg Tyr Phe Ile Pro Ser Gly Trp Arg Ser Gly Asn
            80                      85                      90

ACC AAT TAC GAT TAC GGC GCA ATC GAA CTA AGC GAA CCG ATC GGC AAT        928
Thr Asn Tyr Asp Tyr Gly Ala Ile Glu Leu Ser Glu Pro Ile Gly Asn
        95                      100                     105

ACT GTC GGA TAC TTC GGA TAC TCG TAC ACT ACT TCA TCA CTT GTT GGG        976
Thr Val Gly Tyr Phe Gly Tyr Ser Tyr Thr Thr Ser Ser Leu Val Gly
    110                     115                     120

ACA ACT GTT ACC ATC AGC GGC TAC CCA GGC GAT AAA ACA GCA GGC ACA       1024
Thr Thr Val Thr Ile Ser Gly Tyr Pro Gly Asp Lys Thr Ala Gly Thr
125                     130                     135                     140

CAA TGG CAG CAT TCA GGA CCG ATT GCC ATC TCC GAA ACG TAT AAA TTG       1072
Gln Trp Gln His Ser Gly Pro Ile Ala Ile Ser Glu Thr Tyr Lys Leu
                145                     150                     155

CAG TAC GCA ATG GAC ACG TAC GGA GGA CAA AGC GGT TCA CCG GTA TTC       1120
Gln Tyr Ala Met Asp Thr Tyr Gly Gly Gln Ser Gly Ser Pro Val Phe
            160                     165                     170

GAA CAA AGC AGC TCC AGA ACG AAC TGC AGC GGT CCG TGC TCG CTT GCC       1168
Glu Gln Ser Ser Ser Arg Thr Asn Cys Ser Gly Pro Cys Ser Leu Ala
        175                     180                     185

GTA CAC ACA AAT GGA GTA TAC GGC GGC TCC TCG TAC AAC AGA GGC ACC       1216
Val His Thr Asn Gly Val Tyr Gly Gly Ser Ser Tyr Asn Arg Gly Thr
    190                     195                     200

CGG ATT ACA AAA GAG GTG TTC GAC AAT TTG ACC AAC TGG AAA AAC AGC       1264
Arg Ile Thr Lys Glu Val Phe Asp Asn Leu Thr Asn Trp Lys Asn Ser
205                     210                     215                     220

GCA CAA TAATACACGA AGACAGCCCG CTTCCTTTTG GAACGGGCTG TCACATCTAA        1320
Ala Gln

CGGCCGTATA CTTAATTTCC TTTAAGCCTG TACTTTTTGC CATCTATTGA TATCGTGAAA    1380

TTTGAAGGAC CGCTGATCGG CAAATAATAG ACAAGCTGAA ACTCCGCTTC CTCACCAGGT    1440
```

TTGAATGG                    1448

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: Other nucleic acid
       Synthetic DNA (xi) SEQUENCE DESCRIPTION: SEQ ID NO:2:

ACYAACACYA CYGCTTACCC RTA                    23

(2) INFORMATION FOR SEQ ID NO:3:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: Other nucleic acid
       Synthetic DNA (xi) SEQUENCE DESCRIPTION: SEQ ID NO: 3:

YTTRTCKCCM GGATAKCC                    18

(2) INFORMATION FOR SEQ ID NO:4:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: Other nucleic acid
       Synthetic DNA (xi) SEQUENCE DESCRIPTION: SEQ ID NO: 4:

CAGGAAACAG CTATGAC                    17

(2) INFORMATION FOR SEQ ID NO:5:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: Other nucleic acid
       Synthetic DNA (xi) SEQUENCE DESCRIPTION: SEQ ID NO: 5:

TGTCCCAACA AGTGATGA                    18

(2) INFORMATION FOR SEQ ID NO:6:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: Other nucleic acid
       Synthetic DNA ( x i ) SEQUENCE DESCRIPTION: SEQ ID NO: 6:

AAAACCGTCG CAACAGCC                   18

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 7:

GTTTTCCCAG TCACGAC                    17

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( v ) FRAGMENT TYPE: internal fragment ( v i ) ORIGINAL SOURCE:
        ( A ) ORGANISM: Bacillus licheniformis
        ( B ) STRAIN: ATCC No. 14580

( x i ) SEQUENCE DESCRIPTION: SEQ ID NO: 8:

Gly Tyr Pro Gly Asp Lys
 1              5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( v ) FRAGMENT TYPE: internal fragment ( v i ) ORIGINAL SOURCE:
        ( A ) ORGANISM: Bacillus licheniformis
        ( B ) STRAIN: ATCC No. 14580

( x i ) SEQUENCE DESCRIPTION: SEQ ID NO: 9:

Ala Ile Val His Ile
 1           5

( 2 ) INFORMATION FOR SEQ ID NO:10:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( v ) FRAGMENT TYPE: internal fragment ( v i ) ORIGINAL SOURCE:
        ( A ) ORGANISM: Bacillus licheniformis
        ( B ) STRAIN: ATCC No. 14580

( x i ) SEQUENCE DESCRIPTION: SEQ ID NO: 10:

```
Ser  Thr  Arg  Tyr  Phe  Ile  Pro  Ser
 1              5
```

( 2 ) INFORMATION FOR SEQ ID NO:11:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 11:

GAGTCTAGAG CAGCTGCACA ATAATAG        27

( 2 ) INFORMATION FOR SEQ ID NO:12:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 12:

GAGAAGCTTG ACAGAGAACA GAGAAG        26

( 2 ) INFORMATION FOR SEQ ID NO:13:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 13:

CAAGAATTCG GCTTCCCGTG CGCCTCC        27

( 2 ) INFORMATION FOR SEQ ID NO:14:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid
        Synthetic DNA ( x i ) SEQUENCE DESCRIPTION: SEQ ID NO: 14:

TTGTCTAGAA TTTGCCGATC AGCGGTC        27